United States Patent [19]
Abe et al.

[11] Patent Number: 4,883,863
[45] Date of Patent: Nov. 28, 1989

[54] TRIPEPTIDE DERIVATIVES AND ANTIPLASMIN AGENTS CONTAINING THE SAME

[75] Inventors: Yoshihito Abe; Katsuhiro Yaginuma, both of Koriyama; Takeshi Nagasawa, Urawa; Katsumasa Kuroiwa, Koriyama, all of Japan

[73] Assignee: Nitto Boseki Co., Ltd., Fukushima, Japan

[21] Appl. No.: 247,455

[22] Filed: Oct. 13, 1988

[30] Foreign Application Priority Data

Oct. 30, 1987 [JP] Japan ................. 62-274896

[51] Int. Cl.$^4$ .................. A61K 37/02; C07K 5/08
[52] U.S. Cl. ............................................ 530/331
[58] Field of Search ................. 530/331; 514/18

[56] References Cited

U.S. PATENT DOCUMENTS

| | | | |
|---|---|---|---|
| 4,318,904 | 3/1982 | Shaw et al. | 530/331 |
| 4,452,736 | 6/1984 | Nagasawa et al. | 530/331 |
| 4,658,013 | 4/1987 | Morgan | 530/331 |
| 4,681,871 | 7/1987 | Teschemacher et al. | 530/331 |
| 4,691,007 | 9/1987 | Dutta et al. | |
| 4,703,036 | 10/1987 | Bajusz et al. | 530/331 |
| 4,713,369 | 12/1987 | Stüber | 530/331 |
| 4,740,501 | 4/1988 | DeBarbieri et al. | 530/331 |

FOREIGN PATENT DOCUMENTS 0183271 11/1985 European Pat. Off. .

OTHER PUBLICATIONS

W. Troll et al., "The Action of Plasmin on Synthetic Substrates," J. Biol. Chem., 208 (1964), pp. 85–93.
M. Muramatu et al., "Inhibition of Fabrinolytic Activity . . . ," J. Biochem., 57:3 (1965), pp. 450–453.
S. Fujii, "Synthetic Protease Inhibitors," Taisha, 14:6 (1977), pp. 1087–1098.
T. Aoyama et al., "Synthesis and Structure . . . IV.," Chem. Pharm. Bull. 33:4 (1985), pp. 1458–1471.

Primary Examiner—Lester L. Lee
Attorney, Agent, or Firm—Darby & Darby

[57] ABSTRACT

Tripeptide derivatives of the formula:

A—aaa(B)—Phe—Lys—C         (I)

wherein A, B and C are each one of a specific range of substituents, and aaa, Phe and Lys are each of a specific range of amino acid residues, are potent inhibitors of plasmin and useful for prevention or suppression of hemorrhage and for inhibition of the progress of inflammation.

6 Claims, No Drawings

TRIPEPTIDE DERIVATIVES AND ANTIPLASMIN AGENTS CONTAINING THE SAME

BACKGROUND OF THE INVENTION

1. Field of the Invention

This invention relates to certain pepide derivatives which are useful as selective plasmin inhibitors, for example, for prevention or supression of hemorrhage and for inhibition of the progress of inflammation, and relates to the pharmaceutical use thereof.

2. Description of the Related Art

It has been known that certain derivatives of lysine and arginine have inhibitory activity against plasmin [see, for example, J. Biol. Chem. 208, 85 (1964) and J. Biochem. 57, 450 (1965)].

It has been also known that acetyl-L-leucyl-L-leucyl-lysinal as a tripeptide lysinal has antiplasmin activity [see Japanese patent application Kokai (Laid-Open) No. 47-30618]. These compounds, however, have not been put to practical use as drugs because their plasmin-inhibiting activity is too low.

On the other hand, commercially available proteinase inhibitors such as aprotinin, FOY, Camostat, and Nafamstat also have antiplamin activity [see Taisha, vol. 14, No. 6, p. 1087 (1977) and Chem. Pharm. Bull, vol. 33, No. 4, p. 1458 (1986)]. They, however, are so poor in selectivity that they strongly inhibit also proteases other than plasmin, for example, thrombin and trypsin.

$\epsilon$-Aminocaproic acid and trans-aminoethylcyclohexanecarboxylic acid (t-AMCHA) have been also known as antiplasmin agents, but they inhibit only fibrinolysis by plasmin and have substantially no ability to inhibit decomposition of other substrates by plasmin, e.g., the decomposition of fibrinogen by plasmin (Taisha, vol. 14, No. 6, p. 1087 (1977).

That is to say, as previously described, conventional compounds having plasmin-inhibiting activity are on such a low technical level that they have at least one of the following defects: (1) The activity is very low. (2) The compound is so poor in selectivity that it inhibits also proteases other than plasmin, in particular, thrombin. (3) The compound inhibits only fibrinolysis among actions of plasmins.

SUMMARY OF THE INVENTION

The tripeptides provided with the present invention are those of the formula:

A—aaa(B)—Phe—Lys—C   (I)

wherein A is an alkyloxycarbonyl group, an unsubstituted acyl group, a substituted acyl group having an aryl group as a substituent, a substituted acyl group having an aryloxy group as a substituent, a cycloalkylcarbonyl group, an unsubstituted aroyl group, a substituted aroyl group having an alkyl group as a substituent, a formyl group, a hydrogen atom, an arenesulfonyl group optionally substituted by an alkyl group, a halogen atom, an amine derivative group or an alkyloxy group, or an alkane-sulfonyl group; aaa is a D-lysine residue or a D-tyrosine residue; B is a side-chain substituent of the amino acid residue for aaa which is selected from an aroyl group and an arenesulfonyl group; Phe is a L-phenylalanine residue; Lys is a L-lysine residue or one partly including D-lysine residue; and C is a hydrogen atom, a secondary amino group, or a methyl group having 1 to 3 halogen atoms; a pharmaceutically acceptable acid addition salt thereof, and a pharmaceutically acceptable aldehyde equilibrium derivative thereof in case that C is a hydrogen atom.

DETAILED DESCRIPTION OF THE INVENTION

The above-mentioned compounds of the present invention are potent inhibitors of plasmin. Some of these compounds have the following abilities: (1) strong inhibiting ability, (2) low inhibitory activity against other proteases, in particular, thrombin, (3) inhibitory activity against actions of plasmin other than fibrinolysis. Therefore, they are useful for prevention or suppression of hemorrhage and for inhibition of the progress of inflammation.

The aldehyde equilibrium derivative of the compound of the formula (I) in which C is a hydrogen atom include the bisulfites, hemiacetals and hemiaminals, as well as other masked aldehyde derivatives as described in "The Chemistry of the Carbonyl Group", Vol. 2 in the series "The Chemistry of Functional Groups" Ed. by S. Patai. Interscience Publishers, a division of John Wiley & Sons. New York (1970).

The salts of the compounds of the formula (I) include pharmaceutically acceptable acid addition salts, for example, hydrochlorides, hydrobromides, sulfates, acetates, oxalates, succinates, malates, citrates, lactates, benzenesulfonates, toluenesulfonates and methanesulfonates.

As for A in the formula (I), groups preferred as the alkyloxycarbonyl group are, for example, $C_{1-6}$alkyloxycarbonyl groups such as methoxycarbonyl, ethoxycarbonyl, iso-butoxycarbonyl, pentoxycarbonyl, hexoxycarbonyl, etc.; groups preferred as the unsubstituted acyl group are for example, $C_{2-6}$alkanoyl groups such as acetyl, propanoyl, butanoyl, hexanoyl, etc.; groups preferred as the substituted acyl group having an aryl group as a substituent are, for example, (substituted or unsubstituted phenyl) $C_{2-6}$alkanoyl groups such as phenylacetyl, p-tolyacetyl, etc.; groups preferred as the substituted acyl group having an aryloxy groups as a substituent are, for example, (substituted or unsubstituted phenoxy) $C_{2-6}$alkanoyl groups such as phenoxyacetyl, p-methylphenoxyacetyl, etc.; groups preferred as the cycloalkylcarbonyl group are, for example, $C_5$- or $C_6$-cycloalkylcarbonyl groups such as cyclopentylcarbonyl, cyclohexylcarbonyl, etc.; groups preferred as the unsubstituted aroyl group are, for example, benzoyl, naphthoyl, etc.; groups preferred as the substituted aroyl group having an alkyl group as a substituent are, for example, substituted benzoyl or naphthoyl groups having a $C_{1-6}$alkyl group as a substituent, such as toluoyl, p-ethylbenzoyl, etc. Groups preferred as the arenesulfonyl group are benzenesulfonyl group, naphthalenesulfonyl group, $C_{1-6}$alkyl-substituted benzenesulfonyl or naphthalenesulfonyl groups such as p-toluenesulfonyl and the like; halogen-substituted benzenesulfonyl or naphthalenesulfonyl groups such as p-chlorobenzenesulfonyl and the like, ($C_{2-6}$alkanoylamino)benzenesulfonyl or ($C_{2-6}$alkanoylamino)-naphthalenesulfonyl groups such as p-(acetylamino)-benzenesulfonyl and the like; and $C_{1-6}$alkoxy-substituted benzenesulfonyl or naphthalenesulfonyl groups such as p-methoxybenzenesulfonyl; and groups preferred as the alkanesulfonyl group are, for example, $C_{1-6}$alkylsulfonyl groups such as methanesulfonyl, ethanesulfonyl, butanesulfonyl, etc.

Preferably A is hydrogen atom, formyl group, the $C_{1-6}$alkyloxycarbonyl group, the $C_{2-6}$alkanoyl group, the substituted or unsubstituted phenyl$C_{2-6}$alkanoyl group, the substituted or unsubstituted phenoxy$C_{2-6}$alkanoyl group, the substituted benzoyl group having a $C_{1-6}$alkyl group as a substituent, benzenesulfonyl group, naphthalenesulfonyl group, the $C_{1-6}$alkylsubstituted benzenesulfonyl or naphthalenesulfonyl group, the halogen-substituted benzenesulfonyl or naphthalenesulfonyl group, the $C_{2-6}$alkanoylaminobenzenesulfonyl or $C_{2-6}$alkanoylaminonaphthalenesulfonyl group, or the $C_{1-6}$alkanesulfonyl group.

Preferred groups as the aroyl group for side-chain substituent of aaa in the formula (I) are, for example, benzoyl group, naphthoyl group, and $C_{1-6}$alkyl or halogen-substituted benzoyl or naphthoyl groups such as toluoyl, p-chlorobenzoyl, and the like; and groups preferred as the arenesulfonyl group for side-chain substituent of aaa are benzenesulfonyl group, naphthalenesulfonyl group, and $C_{1-6}$alkyl or halogen-substituted benzenesulfonyl or naphthalenesulfonyl groups such as p-toluenesulfonyl, p-chlorobenzenesulfonyl, and the like. The side-chain substituent is specifically substituted at amino or hydroxy group of the amino acid residue for aaa. The side-chain substituent is preferably benzenesulfonyl group, naphthalenesulfonyl group, and the $C_{1-6}$alkylsubstituted benzenesulfonyl or naphthalenesulfonyl group.

Groups preferred as the secondary amino group for C in the formula (I) are, for example, di-$C_{1-6}$alkylamino groups such as dimethylamino, diethylamino, and the like; and substituted or unsubstituted $C_5$- or $C_6$-cyclic amino groups such as 1-pyrolidinyl, piperidino, 4-benyzlpiperidino, and the like; and groups preferred as the methyl group having 1 to 3 halogen atoms are, for example, methyl group having a halogen atom such as chloromethyl, and the like. C is preferably hydrogen atom, the substituted $C_6$-cyclic amino group or methyl group having a chlorine atom.

Typical and specific examples of the compound of the above general formula (I) of the present invention are as listed in Table 1.

The compound (I) and the pharmaceutically acceptable salt of the present invention can be produced by various methods. The methods are explained below. The following abbreviations are used herein.

Z=benzyloxycarbonyl, DMF=dimethylformamide, AcOH=acetic acid, DMSO=dimethyl sulfoxide, AcOEt=ethyl acetate, NaBH$_4$=sodium borohydride, NaOH=sodium hydroxide, MgSO$_4$=magnesium sulfate, TLC=thin layer chromatography, N=normality, m.p.=melting point, °C.=centigrade, g=gram, ml=milliliter, t=tertiary, p-tosyl=p-toluenesulfonyl, mM=millimolar concentration, mol=molar quantity, Rf=relative mobility in thin layer chromatography, PNA=p-nitroanilide, CHA=3-carboxy-4-hydroxyanilide.

The tripeptide derivatives of the present invention can be synthesized, for example, by deprotection reaction of a corresponding N-substituted-dipeptidy-N-ε-protected-lysine derivative. The protecting group is preferably one which has no adverse effect on the functional group at the carbonyl terminal during the deprotection reaction.

That is to say, a protecting group removable by catalytic reduction is preferred. For example, the tripeptide aldehyde (e.g., Compounds 1 to 11 in Table 1), tripeptide secondary amide (e.g., Compounds 12 in Table 1) and tripeptide chloromethylketone (e.g., Compounds 13 to 26 in Table 1) of the present invention can be prepared by deprotection reaction of a corresponding protected tripeptide aldehyde (IIa), tripeptide secondary amide (IIb) and tripeptide chloromethylketone (IIc), respectively, which are protected with Z group and represented by the formulas:

A—aaa(B)—Phe—Lys(Z)—H        (IIa)

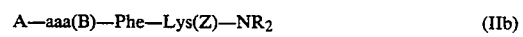

A—aaa(B)—Phe—Lys(Z)—NR$_2$    (IIb)

A—aaa(B)—Phe—Lys(Z)—CH$_2$Cl  (IIc)

wherein two R's in the formula (IIb) are independently alkyl groups, or two R's, taken together, form a cylic alkylene group.

For synthesizing the protected tripeptide aldehyde (IIa), there is employed a method which comprises reducing a corresponding tripeptide ester at a stretch to convert the terminal ester group into a —CH$_2$OH group, and re-oxidizing the reduction product under mild conditions to convert the —CH$_2$OH group into a —CHO group. As for reducing the corresponding tripeptide ester, for example, a tripeptide methyl ester (III) described hereinafter to convert the terminal ester group into —CH$_2$OH, a reducing agent such as sodium borohydride or the like is used. As a solvent, a suitable mixed solvent of water, ethanol, methanol, DMF, etc. is used depending on the solubility of the starting material. Although the reaction temperature is not critical, the reduction is carried out usually with cooling or at room temperature.

As the reaction for oxidizing the —CH$_2$OH group to convert into a —CH=O group, an oxidation reaction using DMSO is particularly effective. For example, the protected tripeptide aldehyde (IIa) can be produced by an oxidation reaction which is carried out by treating the reduction product with pyridine sulfur trioxide in DMSO.

These reactions are represented by reaction formulas as follows.

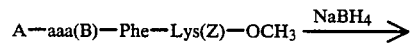

A—aaa(B)—Phe—Lys(Z)—OCH$_3$ $\xrightarrow{\text{NaBH}_4}$

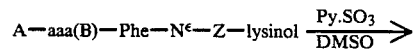

A—aaa(B)—Phe—N$^\epsilon$—Z—lysinol $\xrightarrow[\text{DMSO}]{\text{Py.SO}_3}$

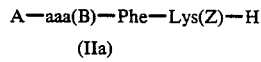

A—aaa(B)—Phe—Lys(Z)—H
(IIa)

N-Substituted-dipeptide-N-εprotected-lysine esters, N-substituted-dipeptidyl-N-ε-protected-lysine-secondary amides (IIb) and N-substituted-dipeptidyl-N-ε-protected-lysine-chloromethylketones (IIc) can be synthesized by a method according to well-known peptide chemistry, for example, the method described in detail in Nobuo Izumiya et al., "Peptide Gosei no Kiso to Jikken" (Basis and Practice of Peptide Synthesis), Maruzen Co., Ltd. (1985)].

As an α-amino protecting group, protecting groups removable by an acid, such as t-butoxycarbonyl group and the like are particularly advantageous. For coupling of two amino acids or coupling of a dipeptide to an amino acid, a peptide bond forming reaction by a conventional stepwise elongation method is employed. For example, a mixed acid anhydride method is employed in which the carbonyl terminal is activated with isobutyl chloroformate. An active ester method (using, for example, N-hydroxysuccinimide, p-nitrophenyl, or 4,6-dimethylpyrimidyl-2-thio) is also advantageous. Active ester derivatives used in the active ester method are prepared advantageously in the presence of a carbodiimide, e.g., N,N'-dicyclohexylcarbodiimide (DCC).

A tripeptide derivatives of the formula (I) in which A is a substituent other than hydrogen atom can be synthesized also by introducing the substituent into the amino terminal of an obtained dipeptidyl-N-protected-lysine derivative of the formula (IV) shown below. The introduction of the substituent can be carried out by reaction of an acid anhydride, an acyl halide, arenesulfonyl chloride, an aroyl halide, an alkanesulfonyl chloride, etc. in a suitable solvent, e.g., DMF, in the presence of a suitable base, e.g., triethylamine (1 to 5 equivalents).

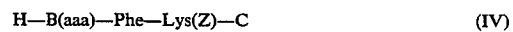

H—B(aaa)—Phe—Lys(Z)—C         (IV)

TABLE 1

The Preferred Compounds of the Present Invention, A—aaa(B)—Phe—Lye—C

| No. | A | aaa(B) | C | Salt | $[\alpha]_D$ | $R_f$(AcOEt: pyridine: AcOH: water = 60:20:6:11) |
|---|---|---|---|---|---|---|
| 1 | iBuOC(=O) | Lys(Me—C6H4—SO2) | H | HCl | $-33.5^{C=0.5}_{DMF}$ | 0.59–0.73 |
| 2 | MeOC(=O) | Lys(Me—C6H4—SO2) | H | HCl | $-38.5^{C=0.5}_{DMF}$ | 0.58–0.70 |
| 3 | Ac | Lys(Me—C6H4—SO2) | H | HCl | $-44.5^{C=0.5}_{DMF}$ | 0.33–0.42 |
| 4 | HC(=O) | Lys(Me—C6H4—SO2) | H | HCl | $-40.0^{C=0.5}_{DMF}$ | 0.38–0.47 |
| 5 | Me—C6H4—SO2 | Lys(Me—C6H4—SO2) | H | HCl | $-23.0^{C=0.5}_{DMF}$ | 0.49–0.58 |
| 6 | 2-naphthyl-SO2 | Lys(Me—C6H4—SO2) | H | HCl | $-32.5^{C=0.5}_{DMF}$ | 0.87–0.95 |
| 7 | H | Lys(Me—C6H4—SO2) | H | 2HCl | $-63.5^{C=0.5}_{DMF}$ | 0.15–0.22 |
| 8 | iBuOC(=O) | Lys(2-naphthyl-SO2) | H | HCl | $-15.5^{C=0.5}_{DMF}$ | 0.47–0.54 |
| 9 | MeOC(=O) | Lys(2-naphthyl-SO2) | H | HCl | $-14.2^{C=0.5}_{DMF}$ | 0.35–0.43 |
| 10 | Me—C6H4—SO2 | Lys(2-naphthyl-SO2) | H | HCl | $-6.5^{C=0.5}_{DMF}$ | 0.45–0.50 |

TABLE 1-continued

The Preferred Compounds of the Present Invention, A—aaa(B)—Phe—Lye—C

| # | A | aaa(B) | C | salt | $[\alpha]_D^{C=0.5, DMF}$ | Rf |
|---|---|---|---|---|---|---|
| 11 | iBuOC(=O) | Lys(Me—C6H4—SO2) | H | HCl | −15.5 | 0.47–0.55 |
| 12 | iBuOC(=O) | Lys(Me—C6H4—SO2) | N-piperidinyl-CH2C6H5 | HCl | −11.0 | 0.57–0.65* (Rf1) |
| 13 | iBuOC(=O) | Lys(Me—C6H4—SO2) | CH2Cl | HCl | −47.0 | 0.50–0.60 |
| 14 | MeOC(=O) | Lys(Me—C6H4—SO2) | CH2Cl | HCl | −49.5 | 0.40–0.50 |
| 15 | CH3C(=O) | Lys(Me—C6H4—SO2) | CH2Cl | HCl | −61.0 | 0.55–0.64 |
| 16 | HC(=O) | Lys(Me—C6H4—SO2) | CH2Cl | HCl | −55.5 | 0.38–0.47 |
| 17 | Me—C6H4—SO2 | Lys(Me—C6H4—SO2) | CH2Cl | HCl | −31.5 | 0.55–0.63 |
| 18 | C6H5—SO2 | Lys(Me—C6H4—SO2) | CH2Cl | HCl | −31.5 | 0.51–0.61 |
| 19 | CH3C(=O)—NH—C6H4—SO2 | Lys(Me—C6H4—SO2) | CH2Cl | HCl | −29.5 | 0.43–0.52 |
| 20 | Cl—C6H4—SO2 | Lys(Me—C6H4—SO2) | CH2Cl | HCl | −34.5 | 0.58–0.67 |
| 21 | H | Lys(Me—C6H4—SO2) | CH2Cl | 2HCl | −70.0 | 0.17–0.27 |
| 22 | Me—C6H4—C(=O) | Lys(Me—C6H4—SO2) | CH2Cl | HCl | −59.0 | 0.47–0.56 |
| 23 | C6H5—O—CH2—C(=O) | Lys(Me—C6H4—SO2) | CH2Cl | HCl | −44.0 | 0.46–0.55 |

TABLE 1-continued

The Preferred Compounds of the Present Invention, A—aaa(B)—Phe—Lye—C

| # | A | aaa(B) | C | salt | [α] | Rf |
|---|---|---|---|---|---|---|
| 24 | PhCH$_2$C(=O)— | Lys(Me—C$_6$H$_4$—SO$_2$) | CH$_2$Cl | HCl | $-50.5_{DMF}^{C=0.5}$ | 0.46–0.55 |
| 25 | CH$_3$SO$_2$ | Lys(Me—C$_6$H$_4$—SO$_2$) | CH$_2$Cl | HCl | $-36.0_{DMF}^{C=0.5}$ | 0.41–0.50 |
| 26 | C$_2$H$_5$SO$_2$ | Lys(Me—C$_6$H$_4$—SO$_2$) | CH$_2$Cl | HCl | $-38.5_{DMF}^{C=0.5}$ | 0.42–0.55 |

| mp | Empirical formula | Elementary analysis value (%) Calcd. (upper values) Found. (lower values) | | |
|---|---|---|---|---|
| | | C | H | N |
| 70–120 | C$_{33}$H$_{50}$N$_5$O$_7$SCl .3/2 H$_2$O | 54.80 54.42 | 7.39 7.25 | 9.68 9.52 |
| 73–110 | C$_{30}$H$_{44}$N$_5$O$_7$SCl .3/2 H$_2$O | 52.89 52.85 | 6.95 6.85 | 10.28 10.09 |
| 77–140 | C$_{30}$H$_{44}$N$_5$O$_6$SCl .3/2 H$_2$O | 54.16 54.11 | 7.12 7.10 | 10.53 10.28 |
| 76–123 | C$_{29}$H$_{42}$N$_5$O$_6$SCl .4/3 H$_2$O | 53.73 53.98 | 6.89 7.04 | 10.80 10.48 |
| 90–110 | C$_{35}$H$_{48}$N$_5$O$_7$S$_2$Cl .5/4 H$_2$O | 54.39 54.41 | 6.59 6.64 | 9.06 9.02 |
| 90–131 | C$_{38}$H$_{48}$N$_5$O$_7$S$_2$Cl .3/2 H$_2$O | 56.10 55.93 | 6.32 6.17 | 8.60 8.53 |
| 81–127 | C$_{28}$H$_{43}$N$_5$O$_5$SCl$_2$ .2H$_2$O | 50.29 50.31 | 7.08 6.90 | 10.47 10.34 |
| 65–70 | C$_{36}$H$_{50}$N$_5$O$_7$SCl .13/10 H$_2$O | 57.21 57.49 | 7.02 6.76 | 9.27 8.92 |
| 75–80 | C$_{33}$H$_{44}$N$_5$O$_7$SCl .5/2 H$_2$O | 53.90 53.74 | 6.71 6.33 | 9.52 9.50 |
| 75–80 | C$_{38}$H$_{48}$N$_5$O$_7$S$_2$Cl .7/10 H$_2$O | 57.12 57.42 | 6.23 6.03 | 8.77 8.31 |
| 55–57 | C$_{36}$H$_{47}$N$_4$O$_8$SCl .5/2 H$_2$O | 55.69 55.63 | 6.75 6.87 | 7.21 7.21 |
| 95–130 | C$_{45}$H$_{64}$N$_6$O$_7$SCl .3/2 H$_2$O | 60.35 60.48 | 7.54 7.80 | 9.38 9.27 |
| 132–135 (dec.) | C$_{34}$H$_{51}$N$_5$O$_7$SCl$_2$ .5/1 H$_2$O | 53.22 52.98 | 7.03 7.05 | 9.13 9.01 |
| 115–125 | C$_{31}$H$_{45}$N$_5$O$_6$SCl$_2$ .H$_2$O | 51.66 51.45 | 6.57 6.64 | 9.71 9.49 |
| 171–174 (dec.) | C$_{31}$H$_{45}$N$_5$O$_6$SCl$_2$ .H$_2$O | 52.84 52.67 | 6.72 6.58 | 9.94 9.63 |
| 85–105 (dec.) | C$_{30}$H$_{43}$N$_5$O$_6$SCl$_2$ .H$_2$O | 52.17 52.02 | 6.57 6.44 | 10.14 10.06 |
| 99–125 (dec.) | C$_{36}$H$_{50}$N$_5$O$_7$S$_2$Cl$_2$ .3/2 H$_2$O | 52.29 52.44 | 6.46 6.20 | 8.46 8.52 |
| 90–115 (dec.) | C$_{35}$H$_{47}$N$_5$O$_7$S$_2$Cl$_2$ .H$_2$O | 52.36 52.72 | 6.15 6.10 | 8.72 8.70 |
| 121–125 (dec.) | C$_{37}$H$_{50}$N$_6$O$_8$S$_2$Cl$_2$ .3/2 H$_2$O | 51.15 50.98 | 6.15 6.07 | 9.67 9.70 |
| 90–122 (dec.) | C$_{35}$H$_{46}$N$_5$O$_7$S$_2$Cl$_3$ .H$_2$O | 50.20 50.31 | 5.79 5.66 | 8.36 8.28 |
| 69–120 (dec.) | C$_{29}$H$_{44}$N$_5$O$_5$SCl$_3$ .3/2 H$_2$O | 49.18 48.96 | 6.69 7.05 | 7.89 10.24 |
| 107–127 (dec.) | C$_{37}$H$_{49}$N$_5$O$_6$SCl$_2$ .H$_2$O | 56.92 56.89 | 6.58 6.50 | 8.97 8.91 |
| 161–163 (dec.) | C$_{37}$H$_{49}$N$_5$O$_7$SCl$_2$ .H$_2$O | 55.77 55.66 | 6.45 6.41 | 8.79 8.54 |
| 133–135 (dec.) | C$_{37}$H$_{49}$N$_5$O$_6$SCl$_2$ .H$_2$O | 56.91 57.16 | 6.58 6.54 | 8.97 8.97 |
| 144–147 (dec.) | C$_{30}$H$_{45}$N$_5$O$_7$S$_2$Cl$_2$ .H$_2$O | 48.64 48.74 | 6.40 6.46 | 7.45 9.28 |
| 166–172 (dec.) | C$_{31}$H$_{47}$N$_5$O$_7$S$_2$Cl$_2$ .H$_2$O | 49.32 49.52 | 6.54 6.55 | 9.28 9.36 |

The compounds of the present invention, as described above, have an excellent inhibitory activity against plasmin, and further are so high in selectivity that they have low inhibitory activity against proteases other than plasmin, for example, thrombin, trypsin, kallikrein and Factor Xa. Therefore, the compounds of the present invention and the pharmaceutically acceptable salts thereof can be used as drugs such as hemostatic agents, anti-inflammatory agents, and the like which are useful in curing hemorrhagic disorders and inflammatory disorders caused by abnomal activation of plasmin.

Both ε-aminocaproic acid and tranexamic acid which are now widely used as antiplasmin agents suppress dissolution of fibrin mass by plasmin and hence are used as useful hemostatic agents and the like. This pharmacological action is considered to be exhibited mainly by attachment of these drugs to the so-called lysine-binding sites (LBS) of plasminogen and plasmin and by resulting inhibition of the drugs on attachment of fibrin to plasminogen and plasmin (see, for example, Chem. Rev. 81, 431 (1981), Biochem. J. 163, 389 (1977), and Eur. J. Biochem. 84, 573 (1978)).

On the other hand, these drugs are only very slightly effective in inhibiting decomposition of synthetic substrates (e.g., PS-994 of NITTO BOSEKI Co., Ltd.) and fibrinogen by plasmin. This fact means that the drugs are not effective in inhibiting decomposition of various substrates for plasmin (eg., fibrinogen) in human organisms other than fibrin.

The compounds of the present invention have a marked inhibitory effect not only on decomposition of fibrin by plasmin but also on decomposition of synthetic substrates and fibrinogen by plasmin. As hemostatic agents and the like, they have an efficacy different from that of the above-mentioned conventional drugs, for example, inhibitory effect on decomposition of fibrinogen. Therefore, said compounds can be used as novel antiplasmin agents.

When the compounds of the present invention are used as drugs, an administration method is not critical. They are formulated into suitable preparations according to conventional pharmaceutical procedures and administered by intravenous injection, intramuscular injection, intravenous infusion, oral administration, etc. A suitable dose of said compound is 1 to 1000 mg per day per recipient. Needless to say, the dose, if necessary, can be properly increased or decreased.

The present invention will be illustrated in more detail in the following examples.

TLC analysis was carried out by use of a silica gel $F_{254}$ plate (mfd. by Merck & Co., Inc.). The following solvents were used as developer:
Rf$_1$; butanol: AcOH: water=4:1:1
Rf$_2$; chloroform: methanol: AcOH: water=80:20:2.5:5
Rf$_3$; chloroform: methanol=10:1
Rf$_4$; chloroform: methanol=5:1
Rf$_5$; chloroform: methanol=20:1

EXAMPLE 1

N-α-Isobutoxycarbonyl-N-ε-(p-tosyl)-D-lysyl-L-phenylalanyl-L-lysinal hydrochloride (1)

(a) L-Phenylalanyl-N-ε-benzyloxycarbonyl-L-lysine methyl ester

N-ε-Benzyloxycarbonyl-L-lysine methyl ester (195.4 g, 0.664 mol) prepared according to the method described in Goorge. R. Pettit, "Synthetic Peptides", vol. 4, p. 314 was dissolved in DMF (1000 ml). N-t-Butyloxycarbonyl-L-phenylalanine-4,6-dimethylpyrimidin-2-yl thiol ester (257.2 g, 0.664 mol) was added in the form of crystals as it was, and the reaction was carried out overnight with stirring at room temperature. The excess of DMF was distilled off, after which AcOEt (3000 ml) was added to the residue and the resulting mixture was washed three times with a cooled 5% aqueous hydrochloric acid solution, once with a saturated aqueous sodium chloride solution, three times with a 10% aqueous sodium hydrogencarbonate solution, and twice with a saturaed aqueous sodium chloride solution. The mixture was dried over MgSO$_4$, concentrated, and then recrystallized from AcOEt-ether to obtain 283.6 g (79%) of N-t-butoxycarbonyl-L-phenylalanyl-N-ε-benzyloxycarbonyl-L-lysine methyl ester as colorless needles. An acetic acid solution containing 2N hydrogen chloride was added to the thus obtained crystals of protected dipeptide (141.8 g, 0.262 mol) with ice-cooling, and the resulting mixture was subjected to reaction at 15° C. for 1 hour. The reaction mixture was poured into ether (5000 ml) with stirring, upon which oil was formed at the bottom of reactor. After 5 hours, the ether was removed by decantation, and AcOEt (5000 ml) was added to the residue to crystallize the residue. The crystals thus formed were collected by filtration and dried to obtain 102.3 g (82%) of the product.

TLC: Rf$_1$=0.46–0.53.

m.p.: 153–155° C.

Elementary analysis for $C_{24}H_{32}N_3O_5Cl$: Calculated: C 60.31, H 6.75, N 8.79%. Found: C 60.59, H 6.86, N 8.80%.

(b) N-α-Isobutoxycarbonyl-N-ε-(p-tosyl)-D-lysine

Isobutychloroformate (30.5 ml, 0.235 mol) was added dropwise to a solution of N-ε-(p-tosyl)-D-lysine (42.5 g, 0.141 mol) in a mixture of methanol (3.5 ml) and a 2N aqueous NaOH solution (141 ml, 0.282 mol) at 0–5° C. over a period of 30 minutes or more while maintaining the pH at 8 with a 2N aqueous NaOH solution, and the resulting mixture were stirred at 0° C. for 2 hours and then at room temperature for 1 hour. The reaction mixture was washed twice with ether, cooled, adjusted to pH2 with a 5N aqueous hydrochloric acid solution, and then extracted with AcOEt. The organic phase was washed three times with a 5% aqueous hydrochloric acid solution and twice with an aqueous sodium chloride solution, dried over MgSO$_4$, and then concentrated to obtain 43.2 g (77%) of the product as a colorless liquid.

TLC: Rf$_2$=0.51–0.54.

(c) N-α-Isobutoxycarbonyl-N-ε-(p-tosyl)-D-lysyl-L-phenylalanyl-N-ε-benzyloxycarbonyl-L-lysine methyl ester Triethylamine (15.0 ml, 0.107 mol) was added to a solution (160 ml) of the L-phenylalanyl-N-ε-benzyloxycarbonyl-L-lysine methyl ester hydrochloride (51.1 g, 0.107 mol) in DMF at −10° C. The resulting suspension was added to the mixed anhydride described below.

N-α-Isobutoxycarbonyl-N-ε-(p-tosyl)-D-lysine (43.0 g, 0.107 mol) was dissolved in DMF (130 ml), and the resulting solution was cooled to −15° C., followed by adding thereto N-methylmorpholine (11.8 ml, 0.107 mol) and then isobutyl chloroformate (13.9 ml, 0.107 mol) at −15° C. After completion of the addition, stirring was continued for 10 minutes, and then the above-mentioned suspension in DMF was added to the resulting mixed anhydride. The resulting mixture was subjected to reaction at −10° C. for 30 minutes and then at 0° C. for 30 minutes. AcOEt (2500 ml) was added and the mixture thus obtained was washed three times with a 5% aqueous hydrochloric acid solution, once with a saturated aqueous sodium chloride solution, three times a 10% aqueous sodium hydrogencarbonate solution and a saturated sodium chloride solution. The mixture was dried over MgSO$_4$, concentrated, and the recrystallized from AcOEt-ether to obtain 70.4 g (80%) of the product.

TLC: Rf$_3$=0.51–0.57.

m.p.: 100–104° C.

Elementary analysis for C$_{42}$H$_{57}$N$_5$O$_{10}$S: Calculated: C 61.22, H 6.97, N 8.50%. Found: C 61.19, H 7.11, N 8.37%.

(d) N-α-Isobutoxycarbonyl-N-ε-(p-tosyl)-D-lysyl-L-phenylalanyl-N-ε-benzyloxycarbonyl-L-lysinol N-α-Isobutoxycarbonyl-N-ε-(p-tosyl)-D-lysyl-L-phenylalanyl-N-ε-benzyloxycarbonyl-L-lysine methyl ester (63.0 g, 0.0765 mol) was dissolved in DMF (230 ml)methanol (765 ml), after which a solution of NaBH$_4$ (57.9 g, 1.53 mol) in water (153 ml) was added dropwise with ice-cooling over a period of 45 minutes or more, and the reaction was carried out overnight with stirring.

After neutralization with AcOH under ice-cooling, the excess of methanol was distilled off, and AcOEt (3450 ml) was added to the residue, after which the resulting mixture was washed three times with a 5% aqueous hydrochloric acid solution, once with a saturated aqueous sodium chloride solution, three times with a 10% aqueous sodium hydrogencarbonate solution and twice with a saturated aqueous sodium chloride solution. The mixture was dried over MgSO$_4$, concentrated, and then recrystallized from AcOEt-ether to obtain 49.6 g (81.4%) of the product, TLC: Rf$_3$=0.29–0.36.

m.p.: 124–126° C.

Elementary analysis for C$_{41}$H$_{57}$N$_5$O$_9$S: Calculated: C 61.87, H 7.22, N 8.80%. Found: C 61.82, H 7.28, N 8.71%.

(e) N-α-Isobutoxycarbonyl-N-ε-(p-tosyl)-D-lysyl-L-phenylalanyl-N-ε-benzyloxycarbonyl-L-lysinal N-α-Isobutoxycarbonyl-N-ε-(p-tosyl)-D-lysyl-L-phenylalanyl-N-ε-benzyloxycarbonyl-L-lysinal (1.00 g, 0.0126 mol) was dissolved in DMSO (5 ml), followed by adding thereto tripropylamine (0.96 ml, 0.0504 mol) and then a solution of pyridine sulfur trioxide (0.80 g, 0.00504 mol) in DMSO (5 ml) at 20° C. or lower. The reaction was carried out with stirring for 15 minutes. The reaction mixture was added to cold water (30 ml) with stirring, and the resulting mixture was extracted with a mixed solvent of AcOEt and ether, after which the AcOEt-ether layer was washed three times with a 10% aqueous citric acid solution, once with a saturated aqueous sodium chloride solution, three times a 10% aqueous sodium hydrogencarbonate solution and three times a saturated aqueous sodium chloride solution. The ether layer was dried over MgSO$_4$, concentrated, and then recrystallized three times from AcOE-ether to obtain 0.85 g (85%) of the product.

TLC: Rf$_3$=0.41–0.51.

m.p.: 105–133° C.

Elementary analysis for C$_{41}$H$_{55}$N$_5$O$_9$S·½ H$_2$O: Calculated: C 61.33, H 7.03, N 8.72%. Found: C 61.32, H 7.12, N 8.64%.

(f) N-α-Isobutoxycarbonyl-N-ε-(p-tosyl)-D-lysyl-L-phenylalanyl-L-lysinal hydrochloride A solution of 9.70% hydrogen chloride (1.14 g, 0.00320 mol) in dioxane and palladium black (1 g) were added to a solution of the N-α-isobutoxycarbonyl-N-ε-(p-tosyl)-D-lysyl-L-phenylalanyl-N-ε-benzyloxycarbonyl-L-lysinal (2.00 g, 0.00252 mol) in DMF (10 ml), and catalytic reduction was carried out in a hydrogen stream at room temperature. After 20 minutes, the catalyst was removed by filtration, and the filtrate was poured into AcOEt (300 ml) and ether was added, upon which an oil was formed at the bottom of reactor. The supernatant was removed by decantation and the residue oil was dried under reduced pressure. The residue was dissolved in a small amount of methanol and reprecipitated with anhydrous ether to obtain 1.32 g (75%) of the desired product.

EXAMPLE 2

N-α-Methoxycarbonyl-N-ε-(p-tosyl)-D-lysyl-L-phenylalanyl-L-lysinal hydrochloride (2)

(a) N-α-Methoxycarbonyal-N-ε-(p-tosyl)-D-lysine

In accordance with the method of Examples 1 (b), by use of N-ε-(p-tosyl)-D-lysine (4.00 g, 0.0133 mol), methanol (3.33 ml) and a 2N aqueous NaOH solution (13.3 ml, 0.0266 mol), 4.54 g (95%) of the product was obtained as a colorless liquid.

TLC: Rf$_2$=0.50–0.55.

(b) N-α-Methoxycarbonyl-N-ε-(p-tosyl)-D-lysyl-L-phenylalanyl-N-ε-benzyloxycarbonyl-L-lysine methyl ester In accordance with the method of Example 1 (c), by use of a solution of L-phenylalanyl-N-ε-benzyloxycarbonyl-L-lysine methyl ester hydrochloride (6.07 g, 0.0127 mol) in DMF (19 ml), triethylamine (1.78 ml, 0.0127 mol), a solution of the N-α-methoxycarbonyl-N-ε-(p-tosyl)-D-lysine (4.54 g, 0.0127 mol) in DMF (15 ml), N-methylmorpholine (1.40 ml, 0.0127 mol) and isobutyl chloroformate (1.65 ml, 0.0127 mol), 6.91 g (70%) of the product was obtained as colourless needles.

TLC: Rf$_3$=0.44–0.53.

m.p.: 86–88° C.

Elementary analysis for C$_{39}$H$_{51}$N$_5$O$_{10}$S: Calculated: C 59.91, H 6.57, N 8.96%. Found: C 59.80, H 6.67, N 8.87%.

(c) N-α-Methoxycarbonyl-N-ε-(p-tosyl)-D-lysyl-L-phenylalanyl-N-ε-benzyloxycarbonyl-L-lysinol In accordance with the method of Example 1 (d), by use of a solution of N-α-methoxycarbonyl-N-ε-(p-tosyl)-D-lysyl-L-phenylalanyl-N-ε-benzyloxycarbonyl-L-lysine methyl ester (5.00 g, 0.00639 mol) in DMF (20 ml)methanol (65 ml), and a solution of NaBH$_4$ (4.83 g, 0.128 mol) in water (13 ml), 4.30 g (89%) of the product was obtained as colorless needles.

TLC: Rf$_4$=0.54–0.60.

m.p.: 161–163° C.

Elementary analysis for C$_{38}$H$_{51}$N$_5$O$_9$S: Calculated: C 60.54, H 6.82, N 9.29%. Found: C 60.23, H 6.86, N 9.24%.

(d) N-α-Methoxycarbonyl-N-ε-(p-tosyl)-D-lysyl-L-phenylalanyl-N-ε-benzyloxycarbonyl-L-lysinal In accordance with the method of Example 1 (e), by use of a solution of N-α-methoxycarbonyl-N-ε-(p-tosyl)-D-lysyl-L-phenylalanyl-N-ε-benzyloxy-L-lysinal (3.70 g, 0.00491 mol) in DMSO (20 ml), tripropylamine (3.73 ml, 0.0196 mol) and a solution of pyridine sulfur trioxide (3.07 g, 0.0196 mol) in DMSO (20 ml), 2.78 g (75%) of the product was obtained as colorless needles.

TLC: Rf$_4$=0.54–0.61.

m.p.: 139–166° C.

Elementary analysis for C$_{38}$H$_{49}$N$_5$O$_9$S·½ H$_2$O: Calculated: C 59.98, H 6.62, N 9.20%. Found: C 60.22, H 6.61, N 9.21%.

(e) N-α-Methoxycarbonyl-N-ε-(p-tosyl)-D-lysyl-L-phenylalanyl-L-lysinal hydrochloride A solution of N-α-methoxycarbonyl-N-ε-(p-tosyl)-D-lysyl-L-phenylalanyl-N-ε-benzyloxy-L-lysinal (1.00 g, 0.00133 mol) in DNF (10 ml) and a solution of 9.7% hydrogen chloride (0.60 g, 0.0016 mol) in dioxane were subjected to reaction in accordance with the method of Example 1 (e). Filtrate obtained after completion of the reaction was poured into AcOEt (250 ml), followed by adding thereto ether, and crystals precipitated were collected by filtration to obtain 0.58 g (67%) of the desired product.

EXAMPLE 3

N-α-Acetyl-N-ε-(p-tosyl)-D-lysyl-L-phenylalanyl-L-lysinal hydrochloride (3)

(a) N-α-t-Butoxycarbonyl-N-ε-(p-tosyl)-D-lysyl-L-phenylalanyl-N-ε-benzyloxycarbonyl-L-lysine methyl ester L-Phenylalanyl-N-ε-benzyloxycarbonyl-lysine methyl ester hydrochloride (23.9 g, 0.050 mol) was dissolved in DMF (100 ml), and a solution of 1.5 N-methylmorpholine in DMF (33.3 ml, 0.050 mol) was added with ice-cooling. The resulting suspension was added to oil of N-ε-t-butoxycarbonyl-N-α-tosyl-D-lysine-4,6-dimethylpyrimidin-2-ylthiol ester (26.13 g, 0.050 mol) to dissolve the oil, followed by stirring overnight at room temperature. After completion of the reaction, AcOEt (2100 ml) was added and the resulting mixture was washed successively three times with a 5% aqueous hydrochloric acid solution, once with a saturated aqueous sodium chloride solution, three times a 10% aqueous sodium hydrogencarbonate solution and twice with a saturated aqueous sodium chloride solution. The mixture was dried over MgSO₄, concentrated, and then recrystallized from AcOEt-ether to obtain 33.2 g (82%) of the product.

TLC: $Rf_5 = 0.32$–$0.43$.

m.p.: 117–120° C.

Elementary analysis for $C_{42}H_{57}N_5O_{10}S$: Calculated: C 61.22, H 6.97, N 8.50%. Found: C 61.30, H 7.18, N 8.53%.

(b) N-ε-(p-Tosyl)-D-lysyl-L-phenylalanyl-N-ε-benzyloxycarbonyl-L-lysine methyl ester hydrochloride An acetic acid solution (80 ml) containing 2N hydrogen chloride was added to N-α-t-butoxycarbonyl-N-ε-(p-tosyl)-D-lysyl-L-phenylalanyl-N-ε-benzyloxycarbonyl-L-lysine methyl ester (32.7 g, 0.0402 mol) with ice-cooling, and the mixture was stirred at 15° C. for 30 minutes. The reaction mixture was poured into ether (2000 ml) and the crystals precipitated were collected by filtration to obtain 25.5 g (85%) of the product.

TLC: $Rf_1 = 0.66$–$0.73$.

m.p.: 120–130° C.

Elementary analysis for $C_{36}H_{50}N_5O_8SCl \cdot H_2O$: Calculated: C 57.09, H 6.73, N 8.99%. Found: C 57.11, H 6.65, N 8.81%.

(c) N-α-Acetyl-N-ε-(p-tosyl)-D-lysyl-L-phenylalanyl-N-ε-benzyloxycarbonyl-L-lysine methyl ester The N-ε-(p-tosyl)-D-lysyl-L-phenylalanyl-N-ε-benzyloxycarbonyl-L-lysine methyl ester hydrochloride (5.24 g, 0.007 mol) was dissolved in DMF (17.5 ml), followed by adding thereto a 1.5N solution (4.67 ml) of N-ethylmorpholine in DMF and the acetic anhydride (3.5 ml) with ice-cooling, and the reaction was carried out with stirring at room temperature for 1 hour. After completion of the reaction, AcOEt (340 ml) was added, and the resulting mixture was washed successively three times with a 5% aqueous hydrochloride acid solution, once with a saturated aqueous sodium chloride solution, three times with an aqueous sodium hydrogencarbonate solution, twice with a saturated aqueous sodium chloride solution and once with a small amount of water. The AcOEt layer was separated and then concentrated, after which ether was added and the crystals precipitated were collected by filtration to obtain 5.07 g (95%) of the product.

TLC: $Rf_3 = 0.25$–$0.31$.

m.p.: 178–181° C.

Elementary analysis for $C_{39}H_{51}N_5O_9S \cdot \frac{1}{2} H_2O$: Calculated: C 60.80, H 6.74, N 9.09%. Found: C 60.85, H 6.79, N 9.06%.

(d) N-α-Acetyl-N-ε-(p-tosyl)-D-lysyl-L-phenylalanyl-N-ε-benzyloxycarbonyl-L-lysinol N-α-Acetyl-N-ε-(p-tosyl)-D-lysyl-L-phenylalanyl-N-ε-benzyloxycarbonyl-L-lysine methyl ester (4.70 g, 0.0614 mol) was reduced in accordance with the method of Example 1 (d) using the corresponding amounts of the reagents and the solvents to obtain 4.20 g (90%) of the product.

TLC: $Rf_3 = 0.18$–$0.21$.

m.p.: 158–160° C.

Elementary analysis for $C_{38}H_{51}N_5O_8S \cdot \frac{1}{2} H_2O$: Calculated: C 61.10, H 7.01, N 9.37%. Found: C 61.36, H 7.08, N 9.41%.

(e) N-α-Acetyl-N-ε-(p-tosyl)-D-lysyl-L-phenylalanyl-N-ε-benzyloxycarbonyl-L-lysinal N-α-Acetyl-N-ε-(p-tosyl)-D-lysyl-L-phenylalanyl-N-ε-benzyloxycarbonyl-L-lysinol (4.00 g, 0.00543 mole) was oxidized in accordance with the method of Example 1 (e) using the corresponding amounts of the reagents and the solvents to obtain 3.22 g (80%) of the product.

TLC: $Rf_3 = 0.51$–$0.56$.

m.p.: 151–159° C.

Elementary analysis for $C_{38}H_{49}N_5O_8S \cdot \frac{1}{2} H_2O$: Calculated: C 61.27, H 6.77, N 9.40%. Found: C 61.24, H 6.84, N 9.31%.

(f) N-α-Acetyl-N-ε-(p-tosyl)-D-lysyl-L-phenylalanyl-L-lysinal hydrochloride

The reaction was carried out in accordance with the method of Example 1 (f) using N-α-acetyl-N-ε-(p-tosyl)-D-lysyl-L-phenylalanyl-N-ε-benzyloxycarbonyl-L-lysinal (1.00 g, 0.00139 mole), DMF (10 ml), a solution of 9.7% hydrogen chloride (0.61 g, 0.00163 mol) in dioxane and palladium black (1.0 g) to obtain 0.73 g (80%) of the desired product.

EXAMPLE 4

N-α-Formyl-N-ε-(p-tosyl)-D-lysyl-L-phenylalanyl-L-lysinal hydrochloride (4)

(a) N-α-Formyl-N-ε-(p-tosyl)-D-lysyl-L-phenylalanyl-N-ε-benzyloxycarbonyl-L-lysine methyl ester Acetic anhydride (10.5 ml) was added to 98% formic acid (31.5 ml) with ice-cooling. The resulting formic anhydride solution was added to a solution prepared as follows. N-ε-(p-Tosyl)-D-lysyl-L-phenylalanyl-N-ε-benzyloxycarbonyl-L-lysine methyl ester hydrochloride (11.2 g, 0.015 mol) was dissolved in DMF (37.5 ml), followed by adding thereto a 1.5N solution (10 ml) of N-ethylmorpholine in DMF with ice-cooling. The formic anhydride solution prepared in the above was added to the resulting solution with ice-cooling. The reaction was carried out overnight at room temperature. The reaction mixture was poured into AcOEt (1120 ml) and the resulting mixture was washed successively three times with a cooled 5% aqueous hydrochloric acid solution, once with a saturated aqueous sodium chloride solution, three times with a 10% aqueous sodium hydrogencarbonate solution and twice with a saturated aqueous sodium chloride solution. The AcOEt layer was dried over MgSO$_4$, concentrated, and then recrystallized from AcOEt-ether to obtain 10.3 g (91%) of the product.

TLC: Rf$_3$=0.24–0.30.

m.p.: 113–116° C.

Elementary analysis for C$_{38}$H$_{49}$N$_5$O$_9$S: Calculated: C 60.70, H 6.57, N 9.31%. Found: C 60.58, H 6.71, N 9.24%.

(b) N-α-Formyl-N-ε-(p-tosyl)-D-lysyl-L-phenylalanyl-N-ε-benzyloxycarbonyl-L-lysinol N-α-Formyl-N-ε-(p-tosyl)-D-lysyl-L-phenylalanyl-N-ε-benzyloxycarbonyl-L-lysine methyl ester (9.90 g, 0.0132 mol) was reduced in accordance with the method of Example 1 (d) using the corresponding amounts of the reagents and the solvents to obtain 9.00 g (94%) of the product.

TLC: Rf$_3$=0.16–0.20.

m.p.: 177–179° C.

Elementary analysis for C$_{38}$H$_{49}$N$_5$O$_9$S·½ H$_2$O: Calculated: C 60.64, H 6.88, N 9.56%. Found: C 60.82, H 6.89, N 9.47%.

(c) N-α-Formyl-N-ε-(p-tosyl)-D-lysyl-L-phenylalanyl-N-ε-benzyloxycarbonyl-L-lysinal N-α-Formyl-N-ε-(p-tosyl)-D-lysyl-L-phenylalanyl-N-ε-benzyloxycarbonyl-L-lysinol (8.00 g, 0.0111 mol) was reacted in accordance with the method of Example 1 (e) using the corresponding amounts of the reagents and the solvents to obtain 7.05 g (88%) of the product.

TLC: Rf$_3$=0.46–0.52.

m.p.: 177–179° C.

Elementary analysis for C$_{38}$H$_{49}$N$_5$O$_8$S·H$_2$O: Calculated: C 60.06, H 6.68, N 9.47%. Found: C 60.26, H 6.80, N 9.28%.

(d) N-α-Formyl-N-ε-(p-tosyl)-D-lysyl-L-phenylalanyl-L-lysinal hydrochloride

N-α-Formyl-N-ε-(p-tosyl)-D-lysyl-L-phenylalanyl-N-ε-benzyloxycarbonyl-L-lysinal (2.00 g, 0.00277 mol) was reduced by addition of a solution of 9.70% hydrogen chloride (1.25 g, 0.00332 mol) in dioxane, in accordance with the method of Example 1 (f) to obtain 1.35 g (78%) of the desired product.

EXAMPLE 5

N-α-N-ε-Di(p-tosyl)-D-lysyl-L-phenylalanyl-L-lysinal hydrochloride (5)

(a) N-α-N-ε-Di(p-tosyl)-D-lysyl-L-phenylalanyl-N-ε-benzyloxycarbonyl-L-lysine methyl ester N-α-(p-Tosyl)-D-lysyl-L-phenylalanyl-N-ε-benzyloxycarbonyl-L-lysine methyl ester hydrochloride (9.58 g, 0.0128 mol) was dissolved in DMF (30 ml), followed by adding thereto a 1.5N solution (17.1 ml) of N-ethylmorpholine in DMF and then p-tosyl chloride (2.44 g, 0.0128 mol) with ice-cooling, and the reaction was carried out at room temperature for 1 hour. After completion of the reaction, AcOEt (940 ml) was added to the reaction mixture and after-treatment was carried out in accordance with the method of Example 1 (c) to obtain 9.99 g (90%) of the product.

TLC: Rf$_3$=0.45–0.54.

m.p.: 84–88° C.

Elementary analysis for C$_{44}$H$_{55}$N$_5$O$_{10}$S$_2$·½ H$_2$O: Calculated: C 59.58, H 6.36, N 7.89%. Found: C 59.87, H 6.39, N 8.03%.

(b) N-α-N-ε-Di(p-tosyl)-D-lysyl-L-phenylalanyl-N-ε-benzyloxycarbonyl-L-lysinal

The title compound was prepared in accordance with the method of Example 1 (d).

TLC: Rf$_3$=0.48–0.54.

m.p.: 76–78° C.

Elementary analysis for C$_{43}$H$_{55}$N$_5$O$_9$S$_2$·½ H$_2$O: Calculated: C 60.11, H 6.57, N 8.15%. Found: C 59.98, H 6.76, N 8.14%.

(c) N-α-N-ε-Di(p-tosyl)-D-lysyl-L-phenylalanyl-N-ε-benzyloxycarbonyl-L-lysinal

The title compound was prepared in accordance with the method of Example 1 (e).

TLC: Rf$_3$=0.54–0.62.

m.p.: 153–159° C.

Elementary analysis for C$_{43}$H$_{53}$N$_5$O$_9$S$_2$: Calculated: C 60.26, H 6.35, N 8.17%. Found: C 60.57, H 6.47, N 8.12%.

(d) N-α-N-ε-Di(p-tosyl)-D-lysyl-L-phenylalanyl-L-lysinal hydrochloride

The desired compound was prepared in accordance with the method of Example 1 (f).

EXAMPLE 6

N-ε-(p-Tosyl)-D-lysyl-L-phenylalanyl-L-lysinal dihydrochloride (7)

(a) N-α-Benzyloxycarbonyl-N-ε-(p-tosyl)-D-lysyl-L-phenylalanyl-N-ε-benzyloxycarbonyl-L-lysine methyl ester A solution of L-phenylalanyl-N-ε-benzyloxycarbonyl-L-lysine methyl ester hydrochloride (22.0 g, 0.046 mol) in DMF (70 ml) and a solution of N-α-benzyloxycarbonyl-N-ε-(p-tosyl)-D-lysine (20.0 g, 0.046 mol) in DMF (55 ml) were subjected to the reaction in accordance with the method of Example 1 (c) using the corresponding amounts of the reagents to obtain 35.3 g (89.4%) of the product.

TLC: Rf$_3$=0.33–0.40.

m.p.: 157–149° C.

Elementary analysis for C$_{45}$H$_{55}$N$_5$O$_{10}$S: Calculated: C 62.99, H 6.46, N 8.16%. Found: C 63.09, H 6.51, N 8.15%.

(b) N-α-Benzyloxycarbonyl-N-ε-(p-tosyl)-D-lysyl-L-phenylalanyl-N-ε-benzyloxycarbonyl-L-lysinol The title compound was prepared in accordance with the method of Example 1 (d).

TLC: Rf$_3$=0.56–0.62.

m.p.: 147–149° C.

Elementary analysis for C$_{44}$H$_{55}$N$_5$O$_9$S: Calculated: C 63.67, H 6.68, N 8.44%. Found: C 63.51, H 6.78, N 8.31%.

(c) N-α-Benzyloxycarbonyl-N-ε-(p-tosyl)-D-lysyl-L-phenylalanyl-N-ε-benzyloxycarbonyl-L-lysinal The title compound was prepared in accordance with the method of Example 1 (e).

TLC: Rf$_3$=0.59–0.66.

m.p.: 123–164° C.

Elementary analysis for C$_{44}$H$_{53}$N$_5$O$_9$S·½ H$_2$O: Calculated: C 63.14, H 6.50, N 8.37%. Found: C 63.33, H 6.45, N 8.37%.

(d) N-ε-(p-Tosyl)-D-lysyl-L-phenylalanyl-L-lysinal-dihydrochloride

The desired compound was prepared in accordance with the method of Example 1 (f).

EXAMPLE 7

N-α-Isobutoxycarbonyl-N-ε-(p-tosyl)-D-lysyl-L-phenylalanyl-L-lysine chloromethyl ketone hydrochloride (13)

(a) L-Phenylalanyl-N-ε-benzyloxycarbonyl-L-lysine chloromethyl ketone hydrochloride A solution (174 ml) containing 2N hydrochloric acid of N-t-butoxycarbonyl-L-phenylalanyl-L-lysine chloromethyl ketone (48.56 g, 0.0897 mol) synthesized by the method of J. R. Coogins, et al. (Biochem. J. 138, 579 (1974) in acetic acid was stirred at 15° C. or lower for 30 minutes. After completion of the reaction, the solution was poured into dried ether (2500 ml) and the crystals precipitated were collected by filtration to obtain 40.81 g (94.8%) of the product.

TLC: $Rf_1 = 0.80$–0.95.

m.p.: 140–144° C.

Elementary analysis for $C_{24}H_{31}N_3O_4Cl_2 \cdot \frac{1}{2} H_2O$: Calculated: C 57.54, H 6.34, N 8.39%. Found: C 57.54, H 6.36, N 8.33%.

(b) N-α-Isobutoxycarbonyl-N-ε-(p-tosyl)-D-lysyl-L-phenylalanyl-N-ε-benzyloxycarbonayl-L-lysine chloromethyl ketone In accordance with the method of Example 1 (c), by use of a solution of the L-phenylalanyl-L-ε-benzyloxycarbonyl-L-lysine chloromethyl ketone hydrochloride (1.99 g, 0.004 mol) in DMF (6 ml), triethylamine (0.56 ml, 0.004 mol), a solution of N-α-isobutoxycarbonyl-N-ε-(p-tosyl)-D-lysine (1.60 g, 0.004 mol) in DMF (8 ml), N-methylmorpholine (0.44 ml, 0.004 mol) and isobutyl chloroformate (0.52 ml, 0.004 mol), 2.58 g (77%) of the product was obtained.

TLC: $Rf_3 = 0.65$–0.70.

m.p.: 172–174° C.

Elementary analysis for $C_{42}H_{56}N_5O_9SCl \cdot \frac{1}{2} H_2O$: Calculated: C 59.24, H 6.75, N 8.23%. Found: C 59.33, H 6.86, N 8.16%.

(c) N-α-Isobutoxycarbonyl-N-ε-(p-tosyl)-D-lysyl-L-phenylalanyl-L-lysine chloromethyl ketone hydrochloride A solution of 9.70% hydrogen chloride (0.45 g, 0.0012 mol) in dioxane and palladium black (1 g) were added to a solution of N-α-isobutoxycarbonyl-N-ε-(p-tosyl)-D-lysyl-L-phenylalanyl-N-ε-benzyloxycarbonyl-L-lysine chloromethyl ketone (0.75 g, 0.00089 mol) in DMF (10 ml), and catalytic reduction was carried out in a hydrogen stream at room temperature. After 3 hours, the catalyst was removed by filtration, after which the filtrate was poured into AcOEt (100 ml) and ether was added. The crystals precipitated were collected by filtration. The crude crystals (0.50 g) thus obtained were subjected to chromatography on Toyo Pearl (HW-40) column and eluted with methanol to obtain 0.18 g (27%) of the desired product.

EXAMPLE 8

The compounds 6, 8 to 12, and 14 to 26 listed in Table 1 were prepared in the same manner as in Example 1 or 7. Analytical values of the compounds obtained were as tabulated in Table 1.

PHARMACOLOGICAL EXPERIMENTS

A concrete explanation regarding the pharmacological activity of the compound provided with the present invention is given below with reference to typical pharmacological experiments for inhibitory activity on several serine proteases and antiplasmin activity. Experimental results for the compounds of the present invention are shown in Table 4 by referring the compound Nos. of Table 1. For comparison, commercially available antiplasmin agents and protease inhibitors having antiplasmin activity, of which structures are shown in Table 2, were also assayed at the same time, and the obtained results for them are shown in Table 3.

Synthetic substrates used for testing the inhibitory activity of the inhibitors on decomposition of substrates by the enzymes were as follows. For plasmin, PS-994 (H—D—Lys(Tos)—Phe—Lys—CHA·2HCl, mfd. by NITTO BOSEKI Co., Ltd.) was used; for thrombin and trypsin, PS-915 (H—D—Phe—Pro—Arg—CHA·2HCl, mfd. by NITTO BOSEKI Co., Ltd.); for Factor Xa, PS-2000 (Z—D—Lys—(HCO)—Gly—Arg—CHA·HCl, mfd. by NITTO BOSEKI Co., Ltd.); and for kallikrein, S-2302 (H—D—Pro—Phe—Arg—pNA, mfd., by Kabi Co., Ltd.).

As plasmin, standard plasmin of Sankyo Color Test $\alpha_2$-D1 Kit was used in an amount of 0.3CU/ml. As thrombin, that of Sankyo Color Test ATIII kit was used in an amount of 1.2 NIHU/ml. As trypsin, that of cord 3703 of Worthington was used in an amount of 2 µg/ml. As human Factor Xa, that of Boehringer Manheim Co., Ltd. was used in an amount of 0.25 U/ml. As human plasma kallikrein, that of Kabi Co., Ltd. was used in an amount of 0.12 U/ml. As terminating color reagents, those for Sankyo Color Test Kit were used. The reactions were carried out at 37° C. unless otherwise specified.

(A)

Determination of inhibitory activity on enzymes using synthetic substrates (i) Plasmin-inhibiting activity Each of aqueous solutions (0.1 ml) of the inhibitors which solutions were various in their respective concentrations was added to 0.4 ml of a buffer solution (a 150 mM aqueous sodium chloride solution containing 100 mM Tris, pH 7.8), and the resulting solution was heated for 5 minutes. To this solution was added 0.2 ml of plasmin solution, followed by incubation for 5 minutes, and then 0.1 ml of a PS-994 solution (10 mM) was added, and then incubated for 5 minutes. After completion of the reaction, 2.0 ml of terminating color reagent was added, and after standing for 10 minutes, absorbance at 700 nm was measured. A concentration of the inhibitor in the reaction system at which the absorbance was one-half that obtained in the absence of the inhibitor was determined as $IC_{50}$. The obtained results are shown in Tables 3 and 4.

(ii) Thrombin-inhibiting activity

Each of aqueous solutions (0.1 ml) of the inhibitors which solutions were various in their respective concentrations was added to 0.4 ml of a buffer solution (a 150 mM aqueous sodium chloride solution containing 150 mM Tris, pH 8.5), and the resulting solution was heated for 5 minutes. To this solution was added 0.2 ml of thrombin solution, followed by incubation for 5 minutes. Then, 0.1 ml of a PS-915 solution (10 mM) was added, followed by incubation for 5 minutes. Thereafter, 2 ml of terminating color reagent was added. After standing for 10 minutes, absorbance at 700 nm was measured, and $IC_{50}$ was determined in the manner described above. The obtained results are shown in Tables 3 and 4.

(iii) Trypsin-inhibiting activity

Each of aqueous solutions (0.1 ml) of the inhibitors which solutions were various in their respective concentrations was added to 0.5 ml of a buffer solution (a 150 mM aqueous sodium chloride solution containing 150 mM Tris, pH 8.0), and the resulting solution was heated for 5 minutes. Then, 0.1 ml of a trypsin solution was added, followed by incubation for 5 minutes. Subsequently, 0.1 ml of a PS-915 solution (10 mM) was added, followed by incubation for 5 minutes. Thereafter, 2 ml of terminating color reagent [containing 2.5 ml/ml of soybean trypsin inhibitor (No. T-9003, available from Sigma Chemical Co.)] was added. After standing for 10 minutes, absorbance at 700 nm was measured and $IC_{50}$ was determined in the manner described above. The obtained results are shown in Tables 3 and 4.

(iv) Factor Xa-inhibiting activity

Each of aqueous solutions (1 ml) of the inhibitors which solutions were various in their respective concentrations was added to 0.3 ml of a buffer solution (a 150 mM aqueous sodium chloride solution containing 50 mM Tris, pH 8.5 ), and the resulting solution was heated for 5 minutes. Then, 0.1 ml of a Factor Xa solution (a 150 mM aqueous sodium chloride solution containing 50 mM Tris and 20 mM calcium chloride, pH 8.5) was added, followed by incubation for 5 minutes. Subsequently, a 5% polyvinyl pyrrobidone solution (0.1 ml) containing 10 mM PS-2000 was added, followed by incubation for 5 min. Thereafter, 2 ml of terminating color reagent was added. After standing for 10 minutes, absorbance at 700 nm was measured and $IC_{50}$ was determined in the manner described above. The obtained results are shown in Tables 3 and 4.

(v) Kallikrein-inhibiting activity

Each of aqueous solutions (0.1 ml) of the inhibitors which solutions were various in their respective concentrations was added to 0.4 ml of a buffer solution (a 150 mM aqueous sodium chloride solution containing 50 mM Tris, pH 8.0), and the resulting mixture was heated for 5 minutes. Then, 0.1 ml of a kallikrein solution [containing 0.5% bovine serum albumin (No. A8022 available from Sigma Chemical Co.)] was added, followed by incubation for 5 minutes. Subsequently, a 10 mM S-2302 aqueous solution (0.1 ml) was added. The reaction was terminated by addition of a 20% aqueous acetic acid solution. Absorbance at 405 nm was measured and $IC_{50}$ was measured in the manner described above. The obtained results are shown in Tables 3 and 4.

(B) Determination of inhibitory activity on plasmin using natural substrates (i) Inhibitory activity on fibrin decomposition by plasmin The determination was carried out by the method of Okamoto et al. (see Keio Journal of Medicine, vol. 11, p. 105 (1962).

Standard human serum (0.1 ml), 0.4 ml of each of 1/20 M potassium phosphate sodium physiological salt buffer solutions (pH 7.4) containing various concentrations of each inhibitor, and 0.1 ml of a solution of streptokinase in physiological saline (1000 U/ml) were stirred and then cooled at 0° C. for 10 minutes. Thereto was added 0.05 ml of a solution of thrombin in physiological saline (100 NIHU/ml, mfd. by Parke Davis Co. Ltd.) at 0° C. After standing for 1 minute, 0.3 ml of a 0.33% solution of bovine fibrinogen (F-4753, available from Sigma Chemical Co.) in physiological saline was added, and the resulting mixture was allowed to stand at 25° C. The solubility was measured every minute by the standard of judgement of Nakamura (see Allergy, vol. 5, p. 1 (1956)) and the time required for complete dissolution was determined. A concentration of the inhibitor at which said time is twice that required in the absence of the inhibitor was determined as $IC_{50}$. The obtained results are shown in Tables 3 and 4.

(ii) Inhibitory activity on fibrinogen decomposition by plasmin

The determination was carried out by a modification of the method described in Takaaki Aoyagi. "Koso Sogai Busshitsu (Enzyme Inhibiting Substances)" Kyoritsu Zensho, p. 12.

To 0.3 ml of phosphate buffer (pH 7.2) was added 0.1 ml of an aqueous solution of each inhibitor, and the resulting solution was heated at 37° C. for 5 minutes. Then, 0.1 ml of a plasmin solution (12 CU/ml) was added, followed by incubation for 5 minutes. Subsequently, 0.7 ml of phosphate buffer (pH 7.2) containing 2% fibrinogen was added, followed by incubation for 15 minutes. After completion of the reaction, a 12% aqueous hydrochloride acid solution (1.5 ml) containing 6% trichloroacetic acid was added, and the resulting mixture was lightly shaken, allowed to stand at room temperature for 15 minutes, and then centrifuged (3000 r.p.m., 10 minutes). The absorbance of the supernatant was measured at 280 nm, and a concentration of the inhibitor at which the absorbance was the same as when the amount of the enzyme added was reduced by half was determined as $IC_{50}$. The obtained results are shown in Tables 3 and 4.

TABLE 2

Commercially Available Antiplasmin Agents and Protease Inhibitors

| Compound No. | Compound |
|---|---|
| A1 | $H_2NCH_2$—⟨hexagon⟩—$CO_2H$ (t-AMCHA) |
| A2 | $C_2H_5OC$(=O)—⟨hexagon⟩—$OC(=O)$—$(CH_2)_5$—$NH$—$C(NH_2)$=$NH \cdot CH_3SO_3H$ (FOY) |

TABLE 2-continued

Commercially Available Antiplasmin Agents and Protease Inhibitors

| Compound No. | Compound |
|---|---|
| A3 | ![structure] (Camostat) |
| A4 | Ac—Leu—Leu—Arg—H.1/2H$_2$SO$_4$.H$_2$O (leupeptin) |
| A5 | ![structure] (Nafamstat) |

TABLE 3

Test Results (Commercially Available Antiplasmin Agents and Protease Inhibitors)

| Compound No. | Synthetic substrate (IC$_{50}$ × 10$^{-7}$ M) | | | | | Natural substrate (IC$_{50}$ × 10$^{-7}$ M) | |
|---|---|---|---|---|---|---|---|
| | Plasmin | Thrombin | Trypsin | Kallikrein | Factor Xa | Fibrin | Fibrinogen |
| A1 | >10$^5$ | >10$^5$ | >10$^5$ | >10$^5$ | >10$^5$ | 86 | >10$^5$ |
| A2 | 400 | 320 | 19 | 45 | 130 | 140 | — |
| A3 | 1.0 | 11 | 0.10 | 0.26 | 550 | 19 | — |
| A4 | 200 | 5900 | 7.8 | 1300 | 140 | 55 | — |
| A5 | 0.28 | 1.2 | 0.01 | 0.0089 | 41 | 2.9 | — |

TABLE 4

Test Results (The Compounds of the Present Invention)

| Compound No. | Synthetic substrate (IC$_{50}$ × 10$^{-7}$ M) | | | | | Natural substrate (IC$_{50}$ × 10$^{-7}$ M) | |
|---|---|---|---|---|---|---|---|
| | Plasmin | Thrombin | Trypsin | Kallikrein | Factor Xa | Fibrin | Fibrinogen |
| 1 | 0.34 | >10$^4$ | 28 | 1.8 | 81 | 2.3 | |
| 2 | 0.079 | >10$^4$ | 25 | 3.6 | 220 | 2.3 | 1.3 |
| 3 | 6.6 | >10$^4$ | 270 | 49 | 2000 | 3.7 | |
| 4 | 0.96 | >10$^4$ | 78 | 10 | 850 | 2.4 | 1.9 |
| 5 | 0.32 | >10$^4$ | 32 | 5.4 | 160 | 7.8 | |
| 6 | 0.16 | >10$^3$ | 35 | 7.9 | 220 | 7.8 | |
| 7 | 1.7 | >10$^4$ | 180 | 9.6 | 1600 | 2.7 | |
| 11 | 0.30 | >10$^4$ | 52 | 29 | 71 | 4.8 | |
| 12 | >10$^4$ | >10$^4$ | >10$^4$ | >10$^4$ | >10$^4$ | 2100 | |
| 13 | 0.31 | 25 | 6.8 | 1.1 | 29 | 4.4 | |
| 14 | 0.033 | 28 | 0.26 | 0.26 | 38 | 1.0 | 0.032 |
| 15 | 0.30 | 150 | 6.6 | 2.2 | 380 | 10.0 | |
| 16 | 0.20 | 100 | 1.5 | 0.43 | 130 | 3.8 | |
| 17 | 0.049 | 16 | 1.2 | 0.38 | 29 | 1.0 | |
| 18 | 0.028 | 31 | 0.60 | 0.31 | 32 | 0.92 | |
| 19 | 0.043 | 25 | 0.87 | 0.50 | 41 | 0.82 | |
| 20 | 0.13 | 14 | 0.58 | 0.32 | 25 | 1.0 | |
| 21 | 0.071 | 78 | 1.3 | 0.46 | 210 | 2.8 | |
| 22 | 0.54 | 34 | 4.8 | 0.58 | 37 | 7.8 | |
| 23 | 0.25 | 20 | 2.2 | 0.20 | 55 | 3.4 | |
| 24 | 1.1 | 78 | 8.9 | 0.71 | 83 | 10.0 | |
| 25 | 0.035 | 2.0 | 0.30 | 0.058 | 13 | 1.1 | |
| 26 | 0.020 | 1.1 | 0.15 | 0.038 | 7.4 | 0.90 | |

As seen from Table 3 and 4, the compounds of the present invention are potent inhibitors on plasmin, have a marked inhibitory effect not only on decomposition of fibrin by plasmin but also on decomposition of fibrinogen by plasmin, and further are so high in selectivity that they have lower inhibitory activity against proteases other than plasmin, for example, thrombin, trypin, kallikrein and Factor Xa.

What we claim is:

1. A tripeptide derivative represented by the general formula:

A—aaa(B)—Phe—Lys—C   (I)

wherein A is an alkyloxycarbonyl group, an unsubstituted acyl group, a substituted acyl group having an aryl group as a substituent, a substituted acyl group having an aryloxy group as a substituent, a cycloalkylcarbonyl group, an unsubstituted aroyl group, a substituted aroyl group having an alkyl group as a substituent, a formyl group, a hydrogen atom, an arenesulfonyl group optionally substituted by an alkyl group, a halogen atom, $C_{2-6}$alkanoyl amino group or an alkyloxy group, or an alkane-sulfonyl group; aaa is a D-lysine residue or a D-tyrosine residue; B is a side-chain substituent of the amino acid residue for aaa which is selected from the group consisting of an aroyl group and an arylsulfonyl group; Phe is a L-phenylalanine residue; Lys is a L-lysine residue or one partly including D-lysine residue; and C is a hydrogen atom, a secondary amino group, or a methyl group having 1 to 3 hydrogen atoms; a pharmaceutically acceptable acid addition salt thereof, and a pharmaceutically acceptable aldehyde equilibrium derivative thereof in case that C is a hydrogen atom.

2. The tripeptide derivative according to claim 1, wherein A is a hydrogen atom, a formyl group, a $C_{1-6}$alkyloxycarbonyl group, a $C_{2-6}$alkanoyl group, a methyl-substituted or unsubstituted phenyl$C_{2-6}$alkanoyl group, a methyl-substituted or unsubstituted phenoxy$C_{2-6}$alkanoyl group, a substituted benzoyl group having a $C_{1-6}$alkyl group as a substituent, a benzenesulfonyl group, a naphthalenesulfonyl group, a $C_{1-6}$alkyl-substituted benzenesulfonyl or naphthalenesulfonyl group, a halogen-substituted benzenesulfonyl or naphthalenesulfonyl group, a ($C_{2-6}$alkanoylamino)benzenesulfonyl or ($C_{2-6}$alkanoylamino)naphthalenesulfonyl group, or a $C_{1-6}$alkylsulfonyl group.

3. The tripeptide derivative according to claim 1, wherein B is a benzenesulfonyl group, a naphthalenesulfonyl group, or a $C_{1-6}$alkyl-substituted benzenesulfonyl or a $C_{1-6}$alkyl-substituted naphthalenesulfonyl group.

4. The tripeptide derivative according to claim 1, wherein C is a hydrogen atom, 1-pyrolidinyl, piperidino, or, 4-benzylpiperidino or a methyl group having 1 to 3 chlorine atoms.

5. The tripeptide derivative according to claim 1, wherein the pharmaceutically acceptable acid addition salt is a hydrochloride, hydrobromide, sulfate, acetate, oxalate, succinate, malate, citrate, lactate, benzenesulfonate, toluenesulfonate, or methanesulfonate.

6. An antiplasmin composition comprising as an active ingredient an effective amount of a tripeptide represented by the general formula:

$$A\text{—}aaa(B)\text{—}Phe\text{—}Lys\text{—}C \qquad (I)$$

wherein A is an alkyloxycarbonyl group, an unsubstituted acyl group, a substituted acyl group having an aryl group as a substituent, a substituted acyl group having an aryloxy group as a substituent, a cycloalkylcarbonyl group, an unsubstituted aroyl group, a substituted aroyl group having an alkyl group as a substituent, a formyl group, a hydrogen atom, an arenesulfonyl group optionally substituted by an alkyl group, a halogen atom, $C_{2-6}$alkanoyl amino group or an alkyloxy group, or an alkane-sulfonyl group; aaa is a D-lysine residue or a D-tyrosine residue; B is a side-chain substituent of the amino acid residue for aaa which is selected from the group consisting of an aroyl group and an arylsulfonyl group; Phe is a L-phenylalanine residue; Lys is a L-lysine residue or one partly including D-lysine residue; and C is a hydrogen atom, a secondary amino group, or a methyl group having 1 to 3 halogen atoms; a pharmaceutically acceptable acid addition salt thereof, or a pharmaceutically acceptable aldehyde equilibrium derivative thereof in case that C is a hydrogen atom the term and a pharmaceutically acceptable carrier.

* * * * *

UNITED STATES PATENT AND TRADEMARK OFFICE
CERTIFICATE OF CORRECTION

PATENT NO. : 4,883,863

DATED : Nov. 28, 1989

INVENTOR(S) : Yoshihito Abe et al.

It is certified that error appears in the above-identified patent and that said Letters Patent is hereby corrected as shown below:

Cover page, left-hand column, field [21]:
Correct the Appl. No. to --257,455--.

Signed and Sealed this

Twenty-fifth Day of June, 1991

Attest:

HARRY F. MANBECK, JR.

*Attesting Officer*    *Commissioner of Patents and Trademarks*